United States Patent
Sano et al.

(10) Patent No.: US 7,060,032 B2
(45) Date of Patent: Jun. 13, 2006

(54) ULTRASONIC DIAGNOSTIC DEVICE, FUNCTION EXTENDING METHOD RELATED TO ULTRASONIC DIAGNOSIS, AND METHOD OF PROVIDING EXTENSION FUNCTION RELATED TO ULTRASONIC DIAGNOSIS

(75) Inventors: Akihiro Sano, Otawara (JP); Keisuke Hashimoto, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/418,135

(22) Filed: Apr. 18, 2003

(65) Prior Publication Data

US 2003/0191389 A1   Oct. 9, 2003

Related U.S. Application Data

(63) Continuation of application No. PCT/JP01/09522, filed on Oct. 30, 2001.

(30) Foreign Application Priority Data

Nov. 1, 2000   (JP) .............................. 2000-334970

(51) Int. Cl.
*A61B 8/00* (2006.01)
(52) U.S. Cl. ..................................... 600/437
(58) Field of Classification Search ............... 600/437, 600/441–447, 459; 367/7, 11, 130, 138; 73/625, 626; 128/916
See application file for complete search history.

(56) References Cited

U.S. PATENT DOCUMENTS

| 5,603,323 | A |   | 2/1997 | Pflugrath et al. |
| 5,722,412 | A | * | 3/1998 | Pflugrath et al. ........... 600/459 |
| 5,897,498 | A |   | 4/1999 | Canfield, II et al. |
| 6,063,030 | A |   | 5/2000 | Vara et al. |
| 6,458,081 | B1 |  | 10/2002 | Matsui et al. |

FOREIGN PATENT DOCUMENTS

| CN | 1192882 A | 9/1998 |
| CN | 1254892 A | 5/2000 |
| DE | 199 11 988 A1 | 9/2000 |
| EP | 0 457 940 | 11/1991 |
| JP | 3-85154 | 4/1991 |
| JP | 9-234201 | 9/1997 |
| JP | 9-285463 | 11/1997 |
| JP | 10-234731 | 9/1998 |
| JP | 11-318906 | 11/1999 |
| JP | 2000-276247 | 10/2000 |
| JP | 2001-258888 | 9/2001 |
| WO | WO 01/70100 | 9/2001 |

* cited by examiner

*Primary Examiner*—Ali Imam
(74) *Attorney, Agent, or Firm*—Oblon, Spivak, McClelland, Maier & Neustadt, P.C.

(57) ABSTRACT

An ultrasonic diagnostic device generates an ultrasonic image based on an echo signal obtained by transmitting/receiving ultrasonic waves to/from a subject body. The device is mobile. The device includes an operation panel to input information related to a location where it is used, a CPU to extract a plurality of extension functions that can be used in the input location among a plurality of extension functions that can be extended at the device, and a display portion to display the extracted plurality of extension functions in order to ask the operator to specify at least one desired function among the extracted plurality of extension functions.

22 Claims, 15 Drawing Sheets

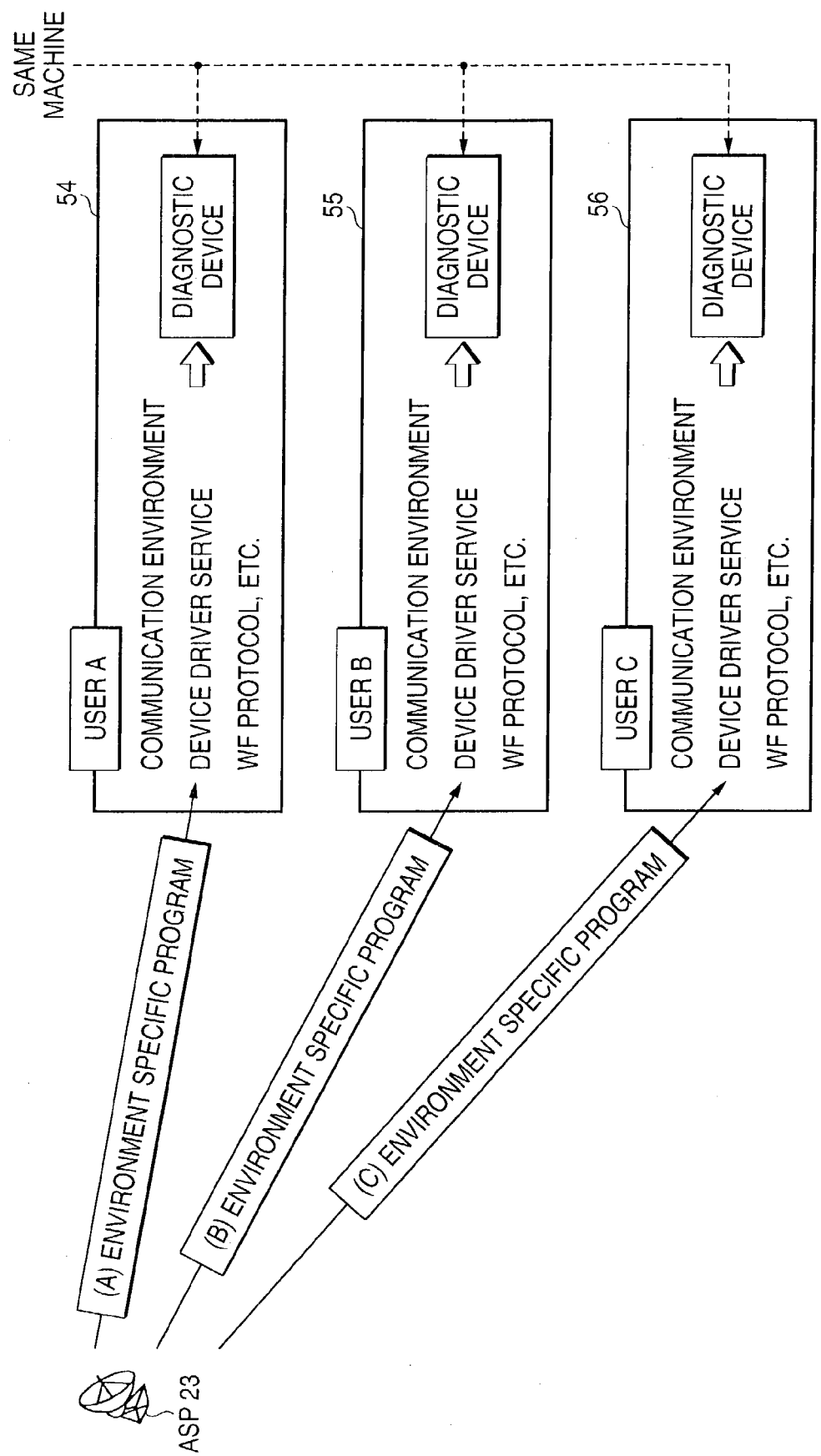

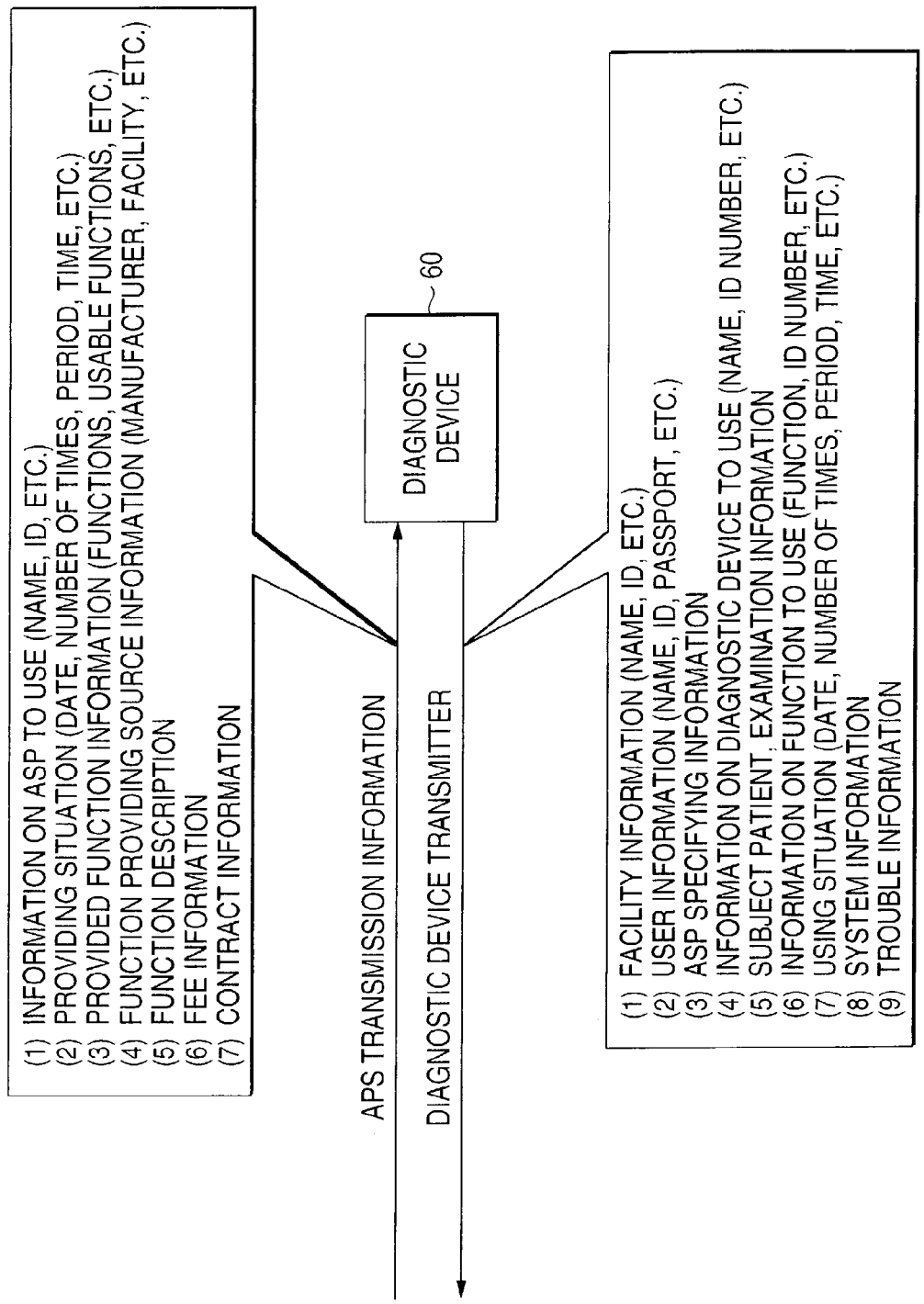

ULTRASONIC DIAGNOSTIC DEVICE, FUNCTION EXTENDING METHOD RELATED TO ULTRASONIC DIAGNOSIS, AND METHOD OF PROVIDING EXTENSION FUNCTION RELATED TO ULTRASONIC DIAGNOSIS

CROSS-REFERENCE TO RELATED APPLICATIONS

This is a Continuation Application of PCT Application No. PCT/JP01/09522, filed Oct. 30, 2001, which was not published under PCT Article 21(2) in English.

This application is based upon and claims the benefit of priority from the prior Japanese Patent Application No. 2000-334970, filed Nov. 1, 2000, the entire contents of which are incorporated herein by reference.

BACKGROUND OF THE INVENTION

1. Field of the Invention

The present invention relates to an ultrasonic diagnostic device that produces images of internal organs or blood streams in a body using ultrasonic waves, a method of extending functions related to ultrasonic diagnosis, and a method of providing extension functions related to ultrasonic diagnosis.

2. Description of the Related Art

Basic techniques of examination using an ultrasonic diagnostic device include B-mode two-dimensional tomography, a Doppler technique referred to as PW or CW mode, a color Doppler technique referred to as CDFM mode for imaging blood streams, a tissue Doppler imaging (TDI) technique for imaging tissue movement, a 3D technique for three-dimensionally displaying tissues, and a 4D technique for dynamically displaying three-dimensional images. The clinical applications include stress echo and contrast echo techniques, and an ACM technique to measure the cardiac output of a heart.

In recent years, ultrasonic diagnostic devices have been reduced in size, some can be carried in a hospital or carried in a vehicle to an outdoor location, and others are portable. When these portable devices are used, the diagnostic application or range is significantly wider than the conventional devices. In an emergency site, during an operation, or for home medical treatment, a nurse or the like can easily carry the device. The users are not only ultrasound specialists among doctors or technicians but could also be rescue workers, nurses or even patients themselves at home unlike the conventional cases.

However, all the functions for these various uses can hardly be implemented in a stationary type ultrasonic diagnostic device. It would be understandably still more difficult to implement these functions in a mobile, compact size ultrasonic diagnostic device because of the weight, the capacity of the memory circuit or the like. Particularly when a mobile ultrasonic diagnostic device is used, it can be carried to a plurality of sections, facilities or locations, but their environments (related to data filing, peripheries, electronic medical charts and the like) are often different, and optimum examination cannot be carried out.

BRIEF SUMMARY OF THE INVENTION

It is an object of the invention to provide an ultrasonic diagnostic device that allows appropriate function extension, a function extension method, and a method of providing the functions.

The ultrasonic diagnostic device generates an ultrasonic image based on an echo signal obtained by transmitting/receiving ultrasonic waves to a subject body. The device is a mobile device. The device includes an input device for inputting information related to a location where the device is used, a function extraction portion for extracting a plurality of extension functions that can be used in the location among a plurality of extension functions that can be extended at the device, and a display portion for displaying the extracted plurality of extension functions in order to ask an operator to specify at least one desired function among the extracted plurality of extension functions.

BRIEF DESCRIPTION OF THE SEVERAL VIEWS OF THE DRAWING

FIG. 18 is a diagram showing another example of how the transmission format is changed depending on the transmission/reception environments of facilities according to the embodiment;

FIG. 19 shows how information is communicated between the diagnostic device and the ASP according to the embodiment;

DETAILED DESCRIPTION OF THE INVENTION

Now, an ultrasonic diagnostic device according to a preferred embodiment of the invention will be described in conjunction with the accompanying drawings. As shown in Table 1, one of the conditions for applying the present invention is that functions necessary in ultrasonic diagnosis are different depending upon the site/environment in which the device is used and who uses the device.

TABLE 1

| Location | Environment | User | Necessary functions |
| --- | --- | --- | --- |
| Medical practitioner | Simple examination with no filling environment | Specialist doctor | Basic functions, Basic measurement |
| | | Non-specialist doctor | Basic functions, Diagnostic navigation function |
| Middle & small hospital | Unique filling enviroment | Doctor | Basic functions, Basic measurements, Unique filling connection function, Diagnostic navigation function |
| Large hospital | HIS/RIS/PACS enviroment | Doctor, technician | Basic functions, Basic measurement, Applied functions, Applied measuring, Applied analysis, DICOM communication function, HL7 communication function, HL7 communication function, Electronic medical chart function |
| | Unique filing enviroment | Doctor, technician | Basic functions, Basic measurements, Applied functions, Applied measuring, Applied analysis, Unique filing connection function |
| Operating room | Scanning to confirm affected | Surgeon | Basic functions, 3D display function |
| Emergency site | Emergency examination | Emergency resuce team | Basic functions, Emergency examination navigation function |
| In ambulance | Emergency examination image/ information communication with hospital | Emergency rescue team, resuce doctor | Basic functions, Emergency examination navigation function, Real time image/ information communication function |
| Satellite hospital | Tele-medicine Tele-operation | Doctor | Basic functions, Basic measurements, Applied functions, Applied measuring, Applied analysis, Examination navigation function, Image/ information communication function |

Figure 1:
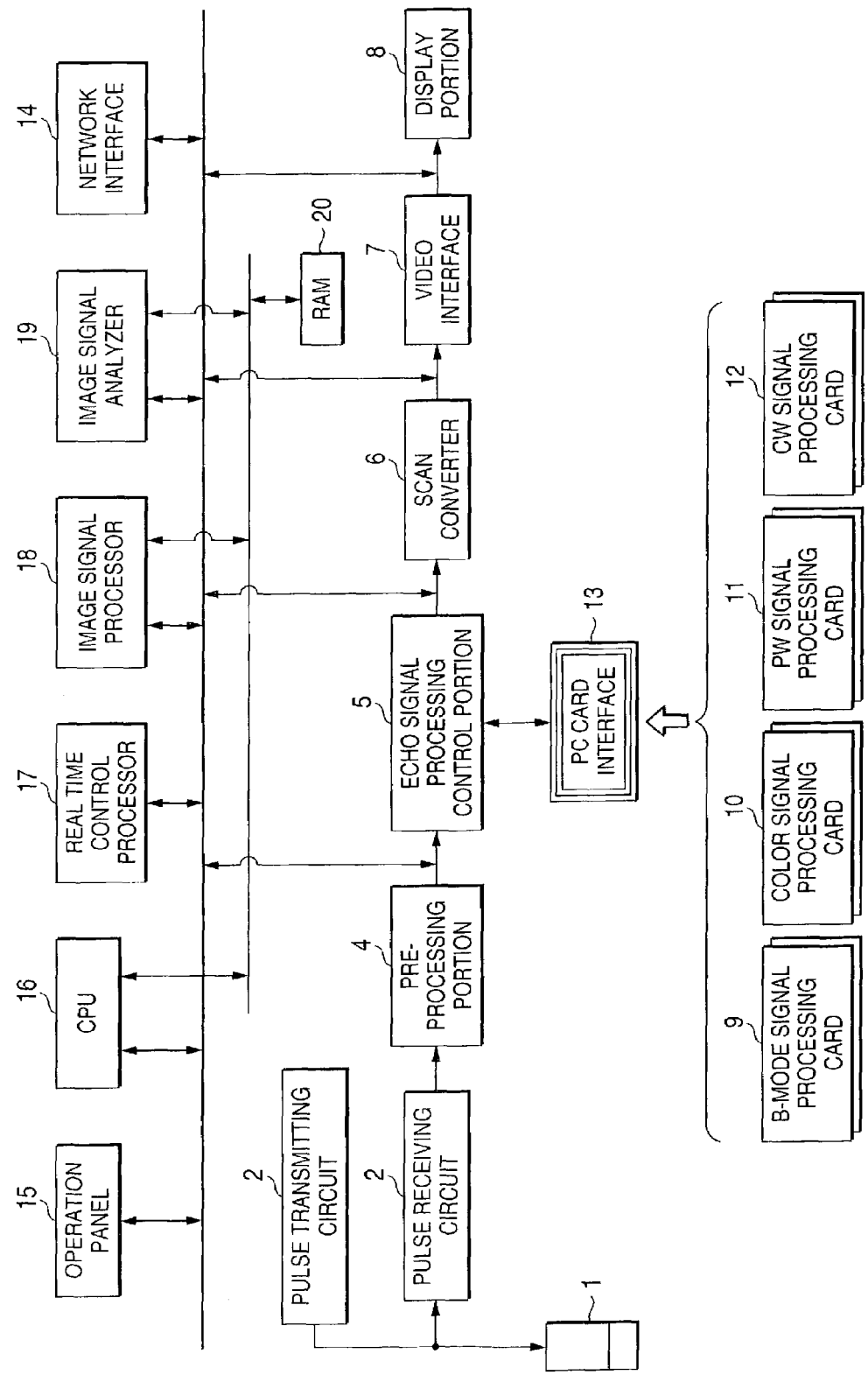
FIG. 1 is a diagram of an ultrasonic diagnostic device according to an embodiment of the invention.

FIG. 1 is a diagram of the configuration of the ultrasonic diagnostic device according to the embodiment of the invention. Now, the echo-pulse system will be described. The device irradiates ultrasonic waves from a pulse transmission circuit 2 into a subject body through an ultrasonic probe 1. Then, echoes reflected by tissues, blood stream and the like in the subject body are received at a pulse receiving circuit 3 through this same probe 1 and demodulated. The received signal is subjected to delay control (phasing addition), filtered or subjected to other processing at a pre-processing portion 4, and then output to an echo signal processing control portion 5 as an echo signal. The echo signal processing control portion 5 carries out various kinds of processing related to image generation to the echo signal input from the pre-processing portion 4. The kinds of processing include transmission/reception operation processing, B mode operation processing, M mode operation processing, color Doppler operation processing, and PW Doppler operation processing, and CW operation processing. The image data produced here is subjected to coordinate transformation or interpolation at a scan converter 6 and then supplied to a video interface 7. The video interface 7 includes a video memory used to display ultrasonic images at a display (monitor) 8. Images are displayed at the monitor 8 based on data written in the memory. The video interface 7 also includes a cine memory used for recording dynamic picture images.

The echo signal processing control portion 5 is provided to carry out processing mainly related image generation to the echo signal, and normally dose not have any processing capability or very limited capability if any. The control portion operates according to an externally provided program file related to image generation and generates image data. The program may be provided through a storage medium such as floppy discs or PC cards (memory cards) 9 to 12. Alternatively, it may be downloaded using a network (wire or wireless electrical communication line). In order to carry out these methods, a PC card interface 13 and a network interface 14 are provided in the device. It is understood that these two methods can be combined. The methods will later be detailed.

Now, the control system will be described. The control system of the device includes an operation panel 15, a CPU 16, a real time control processor 17, an image signal processor 18, an image signal analyzer 19, and a RAM 20. The panel 15 transmits the operator's instructions to the CPU 16. The CPU 16 mainly carries out screen display control, key operation control, internal program file event processing, GUI (Graphical User Interface) processing, network communication processing, data saving processing, report processing and the like.

The real time control processor 17 controls management that requires real time control other than the control of the CPU 16 in particular, and downloads firmware and the like to a programmable device. The image signal processor 18 carries out echo signal recovery or image processing software-wise based on program files such as applications or the like downloaded through the network.

These functions implemented software-wise as described above are implemented based on program files provided through the PC card interface 13 or the network interface 14, which functions are conventionally implemented in other words, through hardware. The image signal analyzer 19 implements clinically necessary application functions. For example, the analyzer executes a tissue Doppler analysis function, an automatic cardiac output calculation processing/analyzing function, or basic analysis, i.e., a curve analysis (FFT analysis, blood stream speed gradient analysis, chronological brightness change analysis), etc. The network interface 14 carries out information exchange with an external server connected wireless or through a wire. The RAM 20 is a memory used for temporary saving or operation by the CPU 16, the real time control processor 17, the image signal processor 18, and the image signal analyzer 19. The memory may be divided into memory spaces for allocation or allocated as a common memory depending upon the configuration. The RAM 20 can store and/or delete program files, setting parameter data, protocol data, drivers, and the like transmitted from an ASP that will be described through the network as required. A magnetic storage device such as a hard disc drive may be used as auxiliary storage means for the RAM 20.

In the above circuit configuration, the functions to be needed can be changed as desired depending upon the environment (location) in which the device is used. When the ultrasonic diagnostic device is a mobile, compact size device, the device may be used in a different environment such as when it is on the move apart from normal patient rooms. In this case, only necessary functions may be downloaded as desired depending upon the environment and installed in the device. More specifically, as the device is lightweight and compact, it can be used in various locations such as different sections and sickrooms or operation rooms in a hospital, other hospitals, an emergency site, in an ambulance, a battle field and the like. The device can be used by various people such as a doctor with requested specialty, an examination doctor, an examination technician, a nurse, a soldier, and a patient himself/herself staying at home. The wide range of use of the device allowed by these features cannot be compared with that of the conventional devices. The optimum functions can be implemented in each case, so that all the requests can be fulfilled. An environment (location) and applicable functions therefor will be described by way of illustration.

Figure 2:
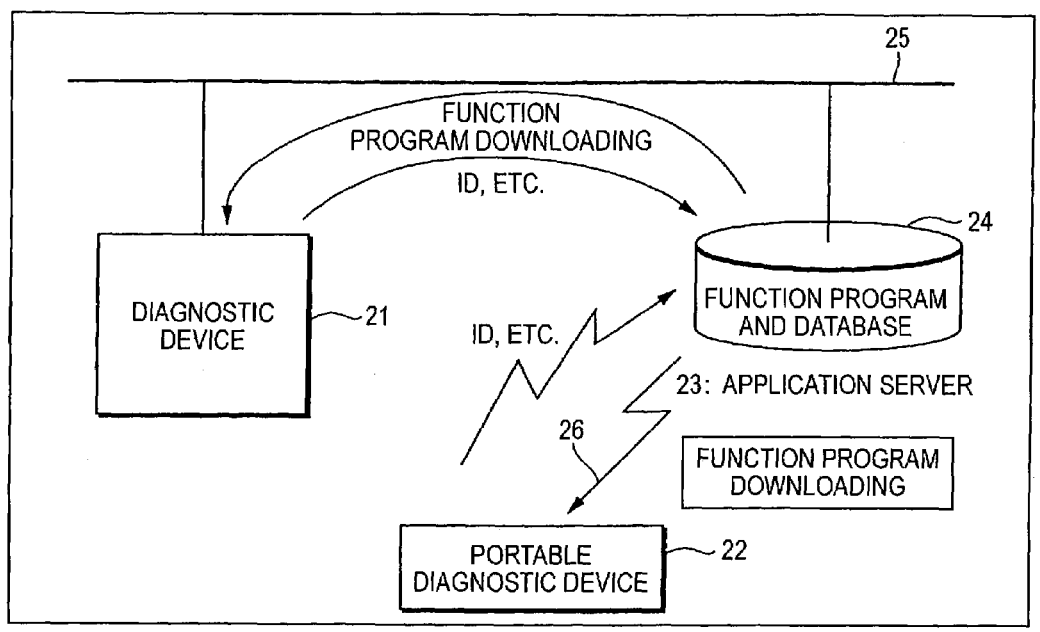
FIG. 2 shows how function program files are downloaded through a network or wireless LAN according to the embodiment.

FIG. 2 shows how necessary processing functions (application program files) are downloaded through a network. Herein, a stationary diagnostic device 21 and a mobile diagnostic device (portable diagnostic device) 22 that can be carried are used. A plurality of application program files supplied from the manufacturer have registered in a database 24 in a server 23 at an application service provider (ASP). When the operator requests the provider to provide a necessary function (application program file) in advance or when the necessity of diagnosis arises. In response to the request, a program file, data, a manual, and the like are downloaded from the application server 23.

In order to download the data, a network must be established with the server 23. The stationary device 21 is typically connected by a wire 25 using Ethernet. Meanwhile, the portable device 22 is suitably connected by a wireless LAN 26. When such a wireless LAN cannot be connected, a medium such as MO and CD, a PC card, a memory card, etc. may be used to supply the data. The medium, the PC card, or the memory card may be directly supplied by the ASP 23 or provided with data in advance from the application server using a terminal such as a LAN connectable PC.

Note that for user log-in the ASP 23 is provided with an ID unique to the ultrasonic diagnostic device, an ID unique to the facility where the ultrasonic diagnostic device is used, and a user ID from the ultrasonic diagnostic device. The ASP 23 is provided with information including the using time, the number of functions used, and the using period from the ultrasonic diagnostic device for charging, gathers information on how the program file is used as statistic information, and calculates billing information based on the gathered statistic information for display and transmission to the user.

Figure 3:
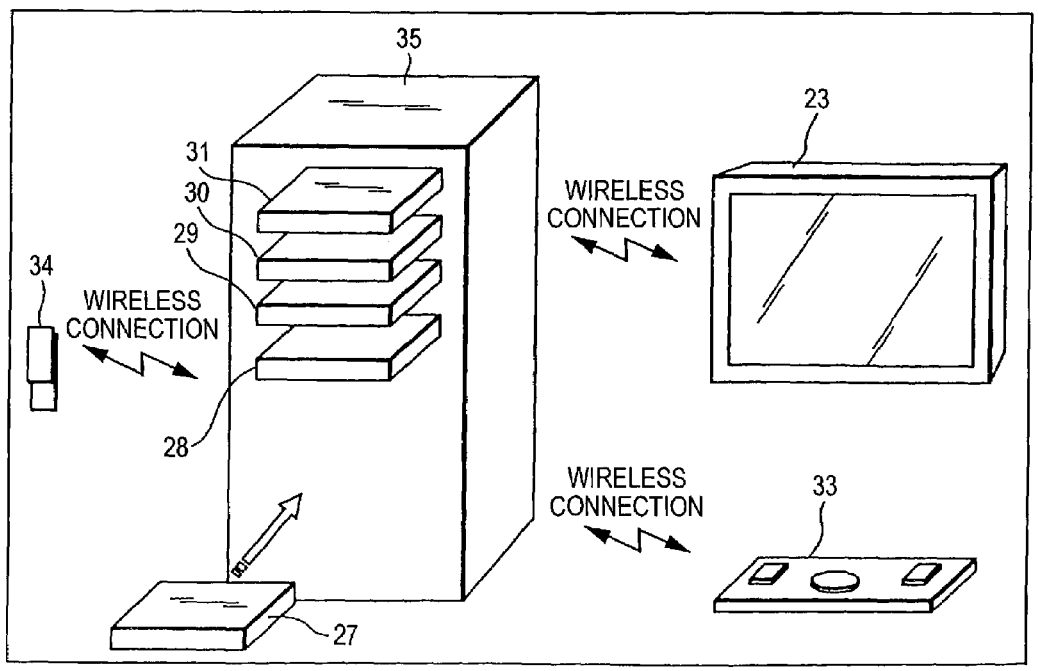
FIG. 3 shows an example of how functions are extended by detachably attaching function extension units according to the embodiment.

Instead of or in combination with being provided with necessary functions through the storage medium or network as described above, the functions may each be formed into a unit as shown in FIG. 3, and a necessary unit may be mounted to the main body of the device. Unlike a conventional combined diagnostic device, separable processing system parts are formed separately for units 27 to 35. In the example in FIG. 3, there are a probe unit 34, a system rack 35, a transmitting unit 31, a receiving unit 30, a 2D ultrasonic image forming unit 29, a color Doppler unit 28, a network unit 27, a monitor unit 32, and an operation unit 33. These units 27 to 35 are connected wireless or by a wire. In the terms of connection, the probe unit 34, the monitor unit 32, and the operation panel unit 33 are basically provided separately from one another and may frequently be relocated, so that wireless connection would basically be preferable for them. The signal processing units 28 to 31 in the main body 35 are connected by a wire or optical communication because high speed data processing is necessary.

Figure 4:
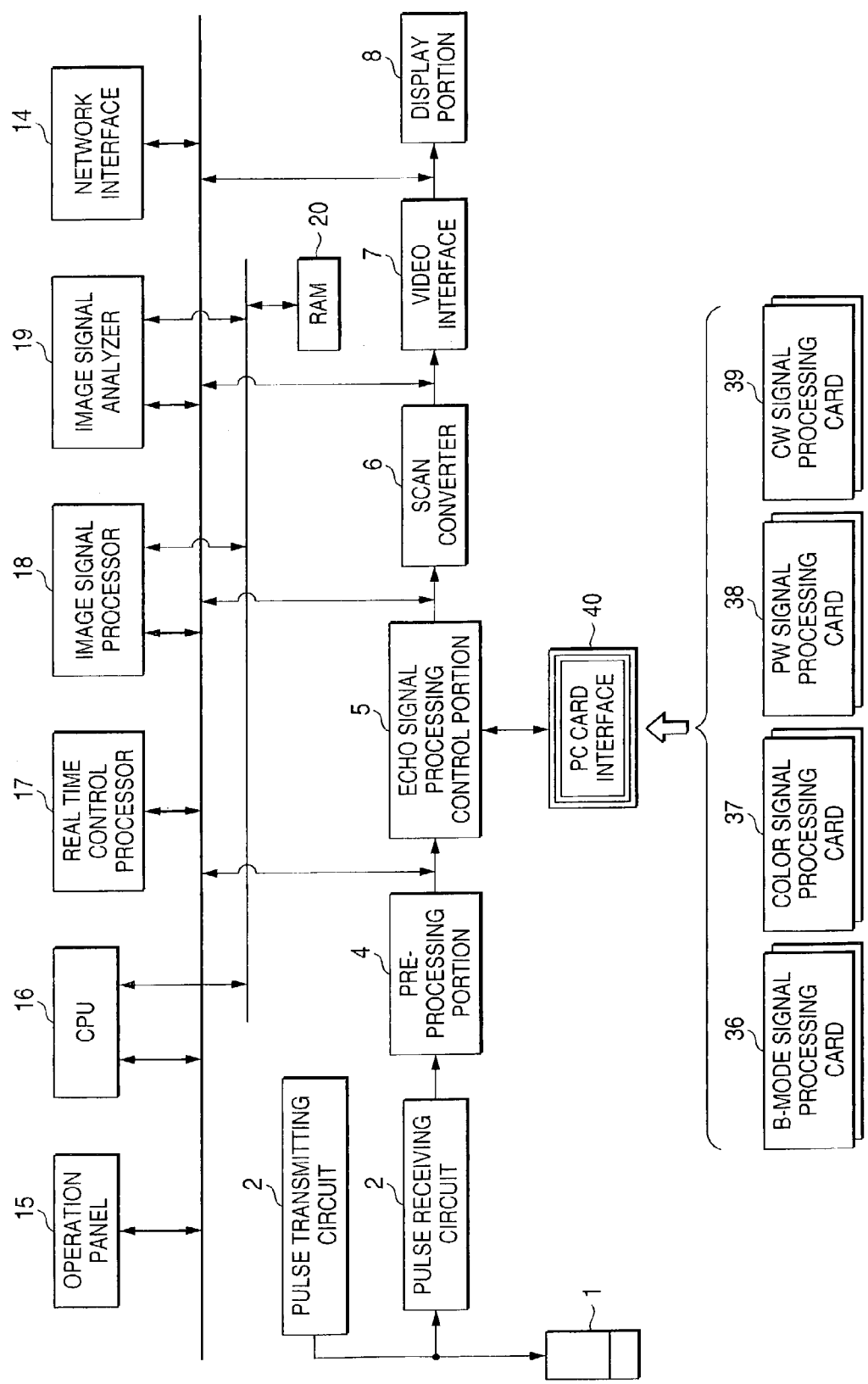
FIG. 4 is a diagram of the configuration of the device shown in FIG. 3.

FIG. 4 is a circuit diagram of a separated type diagnostic device. Herein, the echo signal processing portion is divided into units 36 to 39. The device main body 35 includes a unit interface 40. When one or two desired units among the units 36 to 39 are mounted to the unit interface 40, a necessary function, e.g. an image generating function can be provided to the device. The specification of a bus used for connection of the mounted units is not particularly specified.

Figure 5:
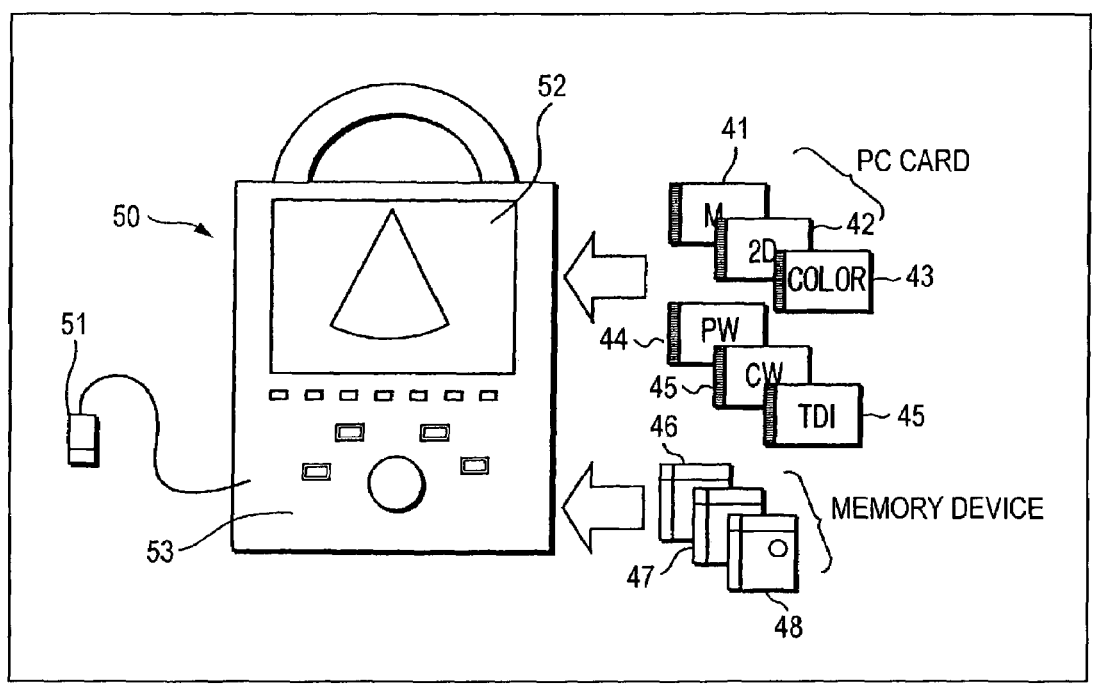
FIG. 5 shows an example of how functions for a portable ultrasonic diagnostic device are extended according to the embodiment.

FIG. 5 is a view showing a compact, portable in particular, diagnostic device whose functions can be extended with a PC card and a memory device. In this device, the main body 50 of the mobile system including a display portion 52, and an operation portion 53 is provided with a special or general-purpose probe 51. When a necessary function is added/changed in the form of hardware, a hard device such as PC cards (PCMCIA) 41 to 45 are used. Meanwhile, when the alteration is carried out software-wise, any of memory devices 46 to 48 such as a floppy disc is used. Firmware for a programmable device such as a DSP and an FPGA in the device or in the PC card may be added/changed using a memory device, etc. Note that any device that can be carried and used for adding hardware may be used instead of the PC card.

Figure 6:
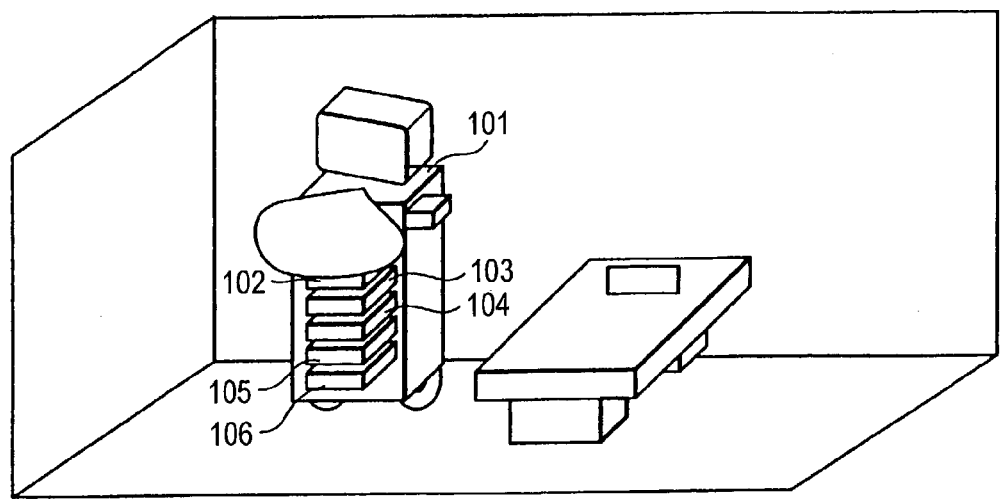
FIG. 6 is a view of a stand-alone type ultrasonic diagnostic device according to the embodiment.
Figure 7:
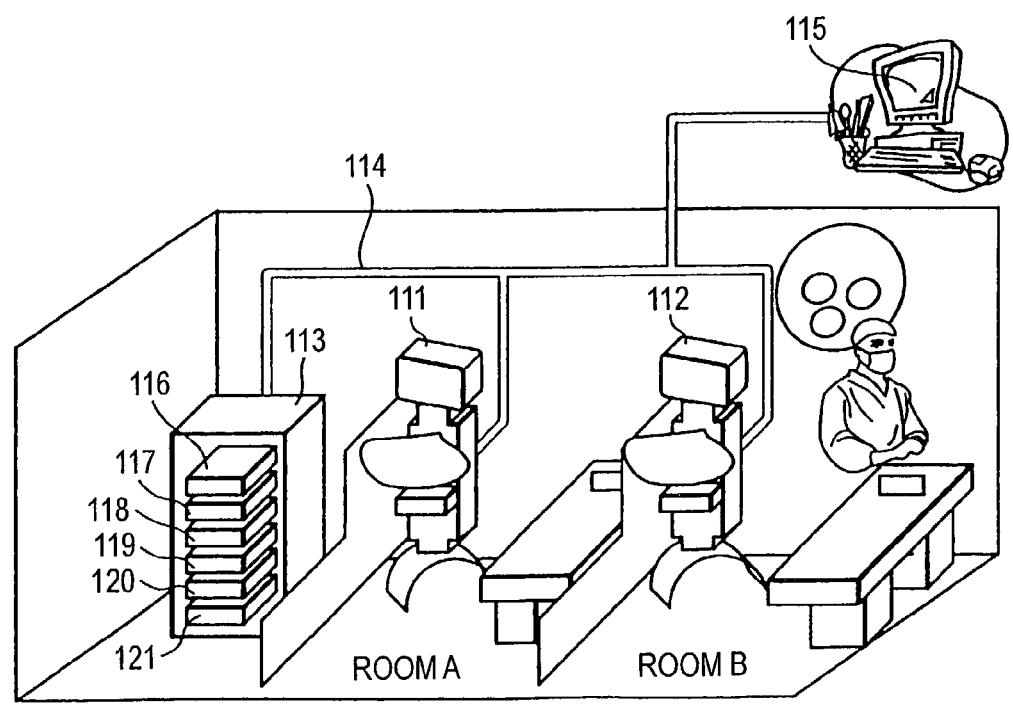
FIG. 7 is a view of a network type ultrasonic diagnostic device according to the embodiment.
Figure 8:
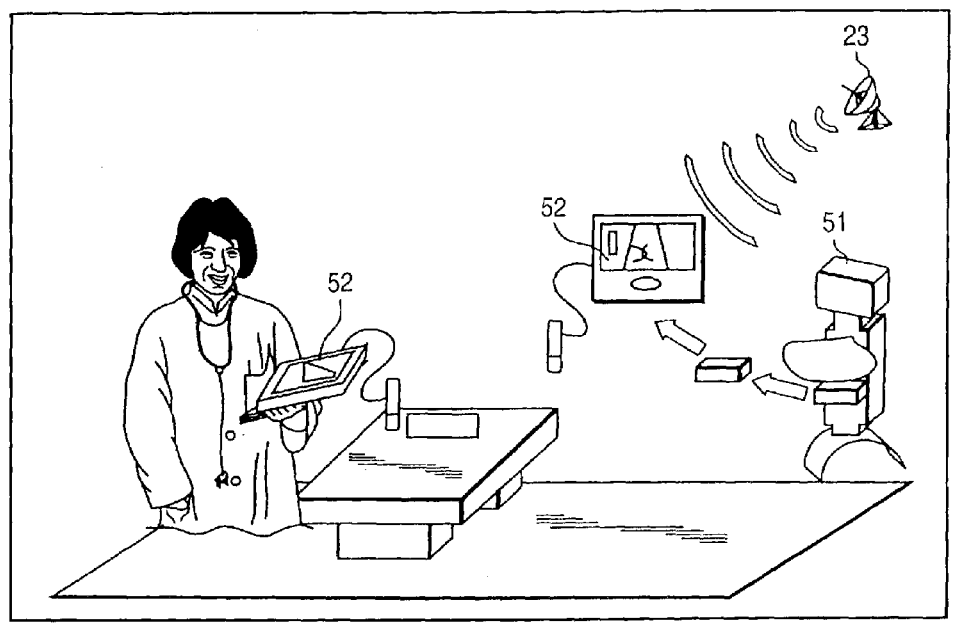
FIG. 8 is a view of a simplified ultrasonic diagnostic device according to the embodiment.

Note that there are various kinds of ultrasonic diagnostic devices, and the invention is applicable to any of such devices. FIG. 6 is a view of a stand-alone type ultrasonic diagnostic device. The main body 101 of the device may be detachably mounted with various units including a transmitting/receiving unit 102, a continuous wave Doppler unit 103, a server unit 104, a network interface unit 105, and a power unit 106. FIG. 7 shows a network type ultrasonic diagnostic device, in which the device main body 113 and the common console 115 are connected through a high speed network 114 to a plurality of device terminals 111 and 112 that can be arranged in separate rooms for receiving ultrasonic waves and displaying images. Ultrasonic echo signals gathered by the device terminals 111 and 112 are sent via the high speed network 114, the device main body 113 carries out signal processing based on the continuous wave Doppler unit 103, and ultrasonic image data, etc. resulting from the processing is returned to the device terminals 111 and 112 via the high speed network 114. The device terminals 111 and 112 display the returned ultrasonic image data at the display. Various units detachably mounted to the device main body 113 include transmitting/receiving units 116 and 117, a continues wave Doppler unit 118, a server unit 119, a network interface unit 120, and a power unit 120. As shown in FIG. 8, a palm size, ultra compact, simplified diagnostic device 52 has the minimum necessary functions for transmission/reception and image generation, and can be detached from the main body 51 and used as it is.

Figure 9:
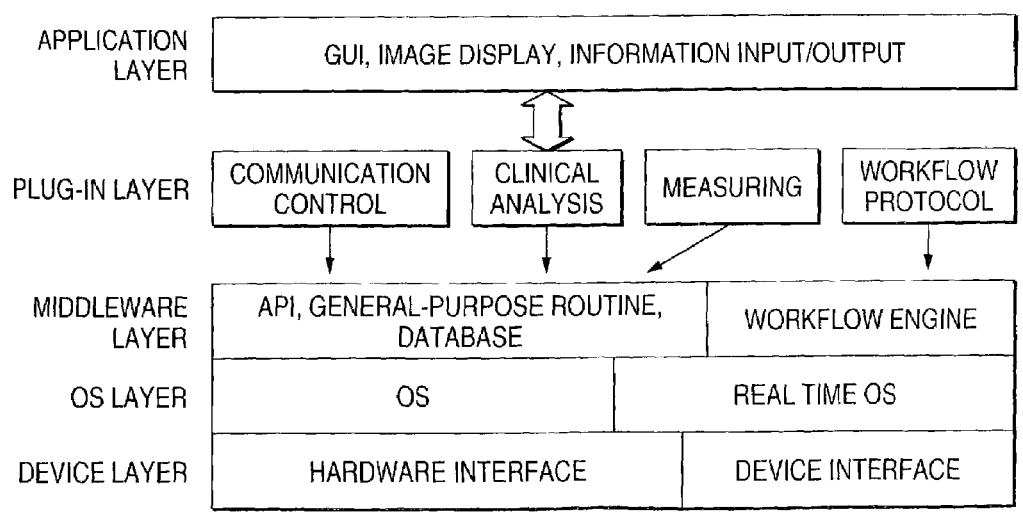
FIG. 9 shows software architecture according to the embodiment.

FIG. 9 is for use in illustration of software architecture according to the embodiment. The device layer is for input/output control for devices connected to the main body such as a probe, a PC card, a memory device, a keyboard, and a track ball. The operating system (OS) layer is a basic program file layer for controlling the device itself. This example uses a general purpose OS for mainly GUI or processing input/output of information, and a real time OS for processing requiring real time management such as control of hardware. The middleware layer includes program file routines based on each application and is used as a library. There are an API for communication between software coded in higher layers and an OS and a general-purpose routine including frequently used functions, a database used for storing/searching image data, examination information, etc. and a workflow engine for automating the operation of the device or behaving like a sequencer to carry out an operation navigation.

The plug-in layer is used to extend an applied routine to the general-purpose middleware layer. The plug-in method is used so that software can be added/changed as desired. For example, this can be achieved by component communication represented by COM, ActiveX provided by the Microsoft Corporation. The application layer mainly includes parts actually operated by the operator such as GUI (Graphical User Interface), and parts for displaying diagnostic images and input/output of information such as examination information and patient information to the diagnostic device.

Figure 10:
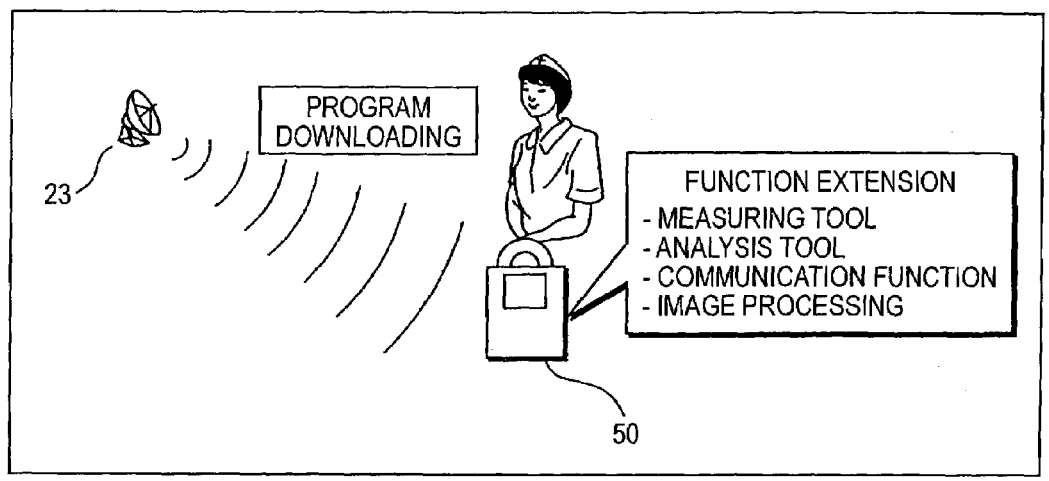
FIG. 10 shows how function program files are downloaded to a mobile system from an application server while the system is on the move according to the embodiment.
Figure 11:
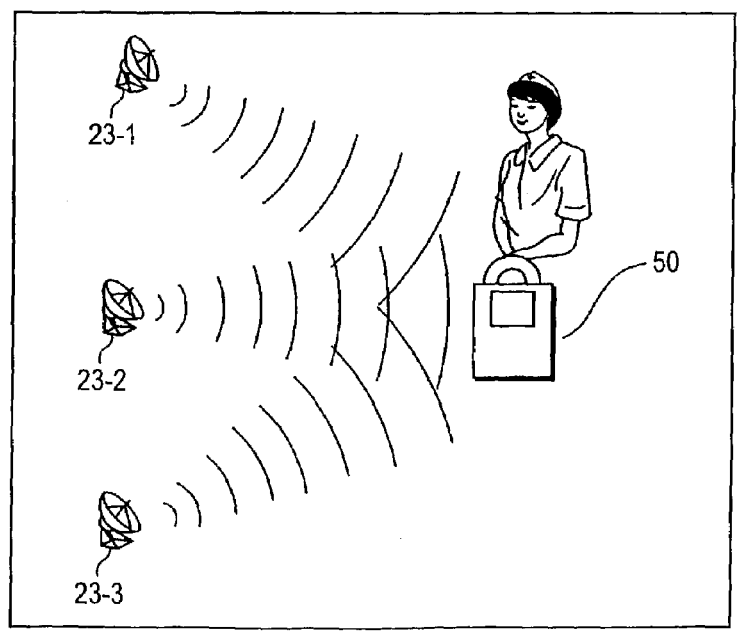
FIG. 11 shows how a plurality of application servers are accessed at a time when necessary functions are provided by a plurality of providers according to the embodiment.

As shown in FIG. 10, in order to extend a necessary function, a program file for the function can be download wireless to the mobile system 50 from the application server 23 even when the device is on the move. As shown in FIG. 11, if the necessary function is provided from a plurality of providers, a plurality of application servers 23-1, 23-2, and 23-3 may be accessed at a time. When the ASP to be used is determined based on the location to use the device (such as the facility), the ASP is automatically switched using the facility information or the like as key information, and optimum program files for the location can be downloaded.

Herein, the ASP 23 can select among a measuring program file, a clinical analysis processing program file, an image processing program file, a communication processing program file, and an examination navigation protocol and can distribute the selected one. For example, when the subject patient suffers from a circulatory disease, circulator specific measuring package software is selected as a measuring program file. The circulator specific measuring package software includes at least one of a left ventricle volume measuring function and a ventricle ejection fraction measuring function. A measuring program file based on the affected part of the subject body can be selected and distributed. When the subject patient suffers from a circulatory disease, circulator specific clinical analysis processing package software is selected as the clinical analysis processing program file. The circulator specific clinical analysis processing package software includes at least one of a tissue Doppler analysis application and an ACM (Automated Cardiac Flow Measurement) application. As the subject patient suffers from a circulatory disease, a circulator specific image processing program file is selected as the image processing program file. In addition, as the subject patient suffers from a circulatory disease, a circulator specific communication processing program is selected. The circulator specific communication processing program allows a dynamic picture image communication protocol and imaging conditions to be transmitted. When the subject patient suffers from a circulatory disease, circulator specific protocols including a screening protocol, an acute cardiac infarction acuity determination protocol, and a confirmation protocol after a coronary revascularization operation are selected as the examination navigation protocols. The examination navigation protocols allow control of the operation of the device according to a pre-defined diagnostic procedure, and change control of the device depending upon the progress of the examination.

The ASP 23 is provided with information related to the environment (location) of the diagnostic device from the device itself, and extracts at least one of a plurality of extension functions that can be used in the location based on the input environment. A program file related to at least one of the measuring program file, the clinical analysis processing program file, the image processing program file, the communication processing program file, the examination navigation protocol is selected depending upon the location, and the selected program file can be transmitted to the ultrasonic diagnostic device.

The ASP 23 is provided with information related to the environment in which the diagnostic device is used from the device itself, and selects a program file related to at least one of a communication processing program file saving program file, a peripheral driver, and an examination navigation protocol based on the input environment. Note that the environment information may be manually input from the operation portion of the ultrasonic diagnostic device, or may be automatically obtained based on a signal from radio identifying signal generation means that is separately provided as will be described. In addition, the ASP 23 is provided with information related to the environment in which the ultrasonic diagnostic device is used from the device and can select a device driver for a printer, a saving device, a communication device, and the like depending upon the input environment. The ASP 23 is provided with information related to the environment in which the ultrasonic diagnostic device is used from the device, selects an examination navigation protocol based on the input environment and can transmit the selected protocol to the ultrasonic diagnostic device. Note that in the above description, the ASP 23 determines the program files, the setting information, and the protocols to be used based on the disease or environment information. These program files, the setting information, and the protocols, to be used can be determined on the ultrasonic diagnostic device based on the disease or environment information, and the determined program files, setting information and protocols may be read from the ASP 23. The ultrasonic diagnostic device deletes program files, protocols and the like that have been stored in the RAM 20, and stores the new program files, protocols and the like transmitted from the ASP 23 in the internal storage means. The ultrasonic diagnostic device changes selectable function items to be displayed on the screen of the device depending on these program files and protocols. In this way, the selectable function items to be displayed on the screen of the ultrasonic diagnostic device are changed depending on the disease or the environment among the contents as in the above Table 1 as required, and therefore a doctor in charge can examine smoothly without any trouble in selection. Program files stored by the storage means on the ultrasonic diagnostic device are deleted as required and exchanged with necessary program files, so that the storage capacity of the device may be small and the structure of the device can be simple.

Figure 12:
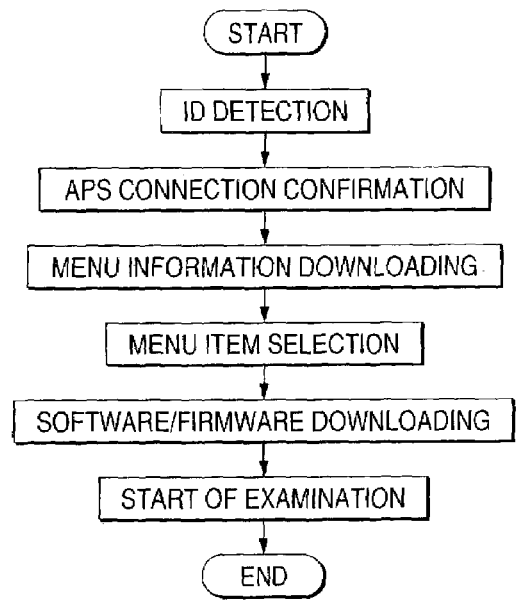
FIG. 12 is a chart showing a basic procedure by connection with an application server according to the embodiment.

FIG. 12 shows a basic procedure started by connection with the application server 23. The operator transmits a connection request to the application server 23 and the ID information by operating the device. The ASP 23 inquires about the ID and the like, permits the operator to log in, and specifies the range of use by the operator that is predetermined by a license contract with the operator. More specifically, if the signed license contract covers level 1, for example, all the function program files prepared by the server 23 can be provided. To a user with the license contract covering level 2, only a limited part of the functional program files prepared by the server 23 can be provided.

The log-in procedure may be automatically carried out once the power is turned on for the device. Then, in order to extend and change functions, function menu information registered on the server side is downloaded. The operator selects necessary functions. In this procedure, using previously known information such as facility information, patient information, disease information, and examination reservation information as key information, the functions may be automatically selected for a menu. Then, after the selected functions are downloaded, examination can be started.

Figure 13:
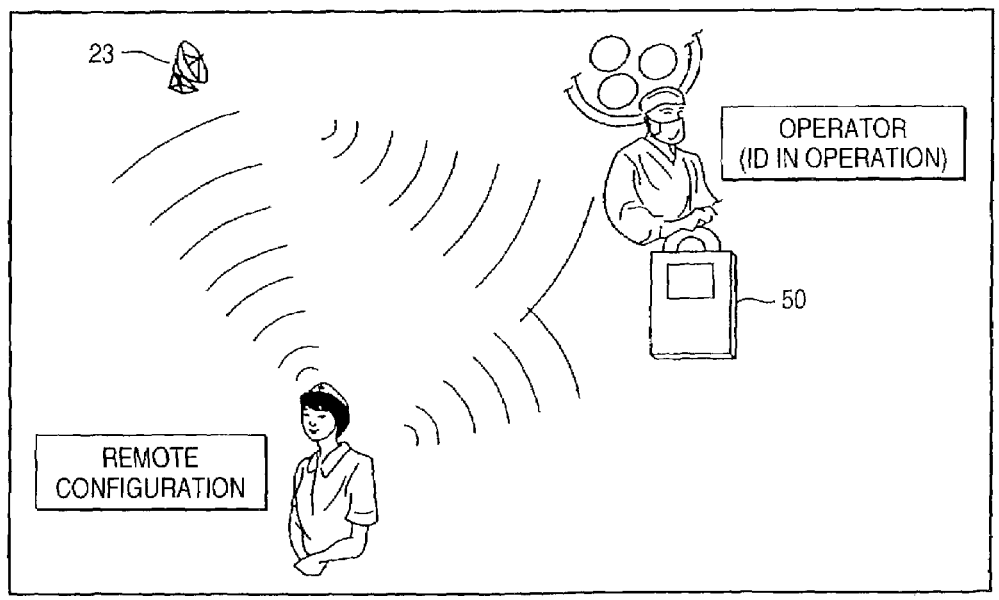
FIG. 13 is a view of how exchange between a technician or doctor only in charge of examination and a server is taken over by another person according to the embodiment.
Figure 14:
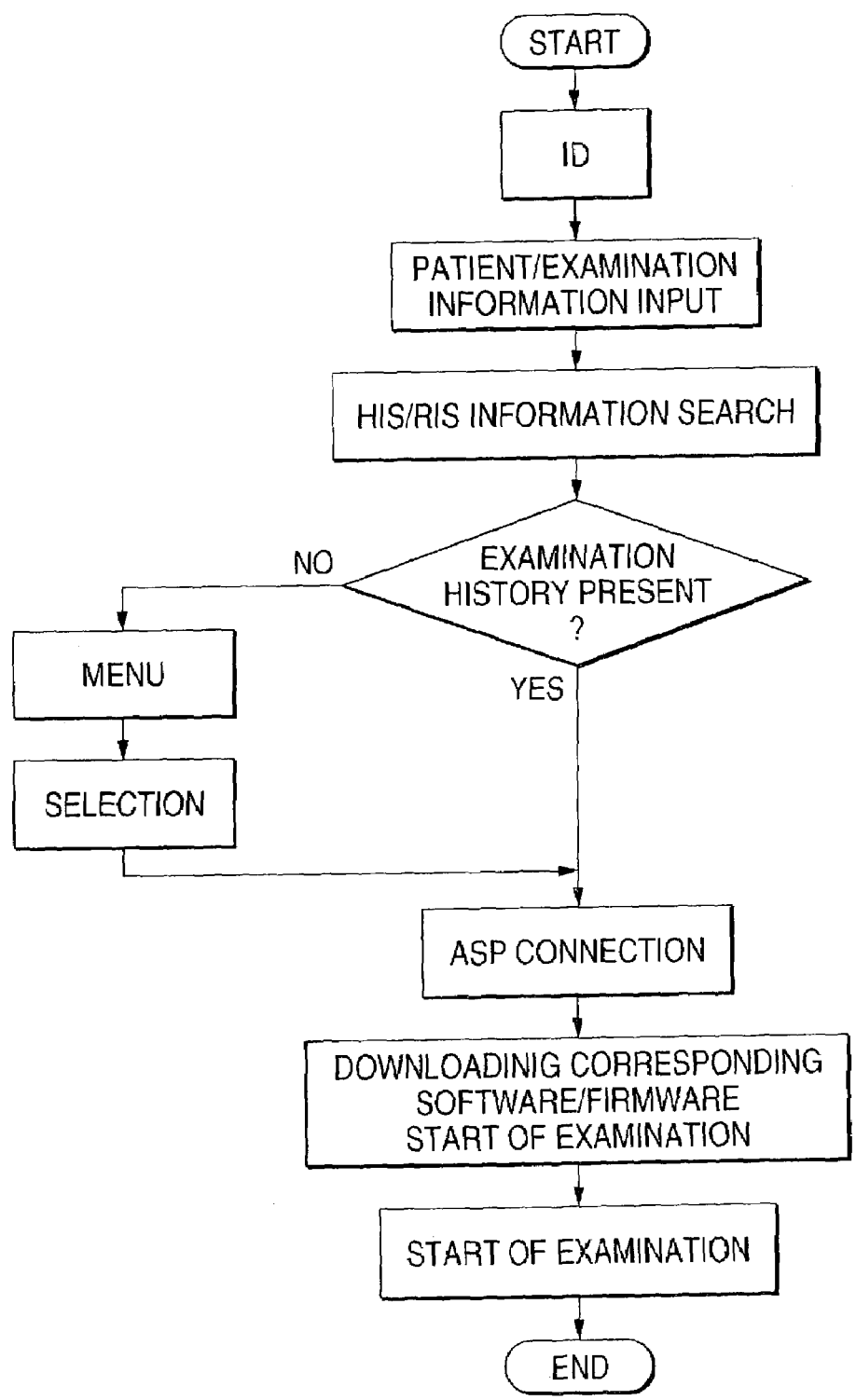
FIG. 14 is a chart showing a procedure to automatically provide function program files used in the past according to the embodiment.

Note that the procedure (configuration) does not have to be carried out by the operator who actually operates the device. FIG. 13 shows an example of how a technician or doctor can only be in charge of examination while another person takes care of exchanges with the server. The configuration can also be operated from a remote location. As shown in FIG. 14, when patient information or examination information is input, the information is used as key information to find information such as HIS (Hospital Information System) and RIS (Radiology Information System) by searching. As a result, when there is an examination history for the patient, the device is connected with the server 23 and software/firmware related to the function(s) used for the examination(s) in the past is automatically downloaded from the server 23, so that the necessary condition for the start of examination is satisfied. Meanwhile, when there is no such examination history for the patient, software/firmware for necessary functions is specified by menu selection, and the selected software/firmware is downloaded from the server 23.

Figure 15:
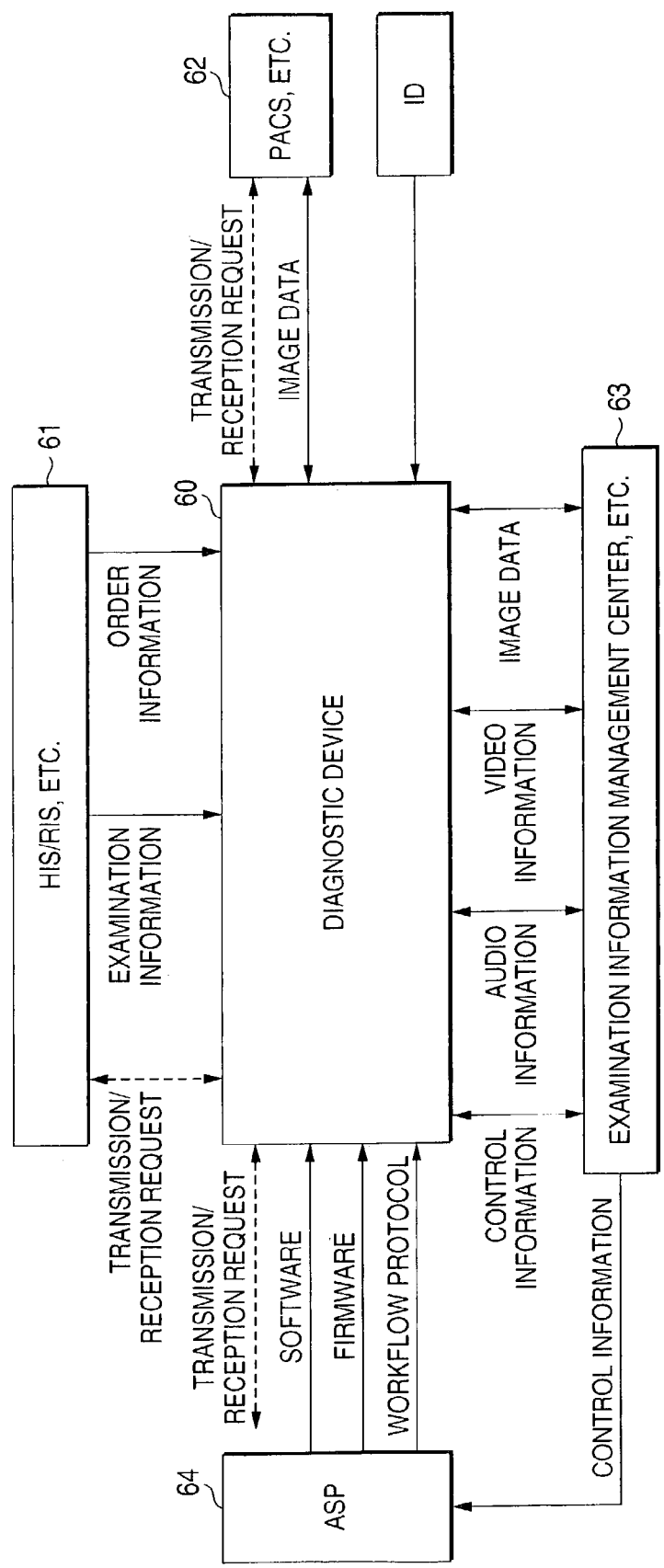
FIG. 15 is a diagram showing how information is exchanged between the ultrasonic diagnostic device and externally provided HIS/RIS, PACS, examination information management center, and ASP according to the embodiment.

FIG. 15 shows how information is exchanged between the ultrasonic diagnostic device 60 and externally provided HIS/RIS 61, PACS 62, examination information management center 63 and ASP 64. Requests of transmission/reception, examination information, order information, and the like are exchanged between the device and the HIS/RIS 61. Requests of transmission/reception, image data and the like are exchanged between the device and the PACS 62. Control information, audio information, video information, image data, and the like are exchanged between the device and the examination information management center 63. As described above, requests of transmission/reception, software (program files), firmware, a workflow protocol (examination procedure), and the like are exchanged between the device and the ASP 64.

Figure 16:
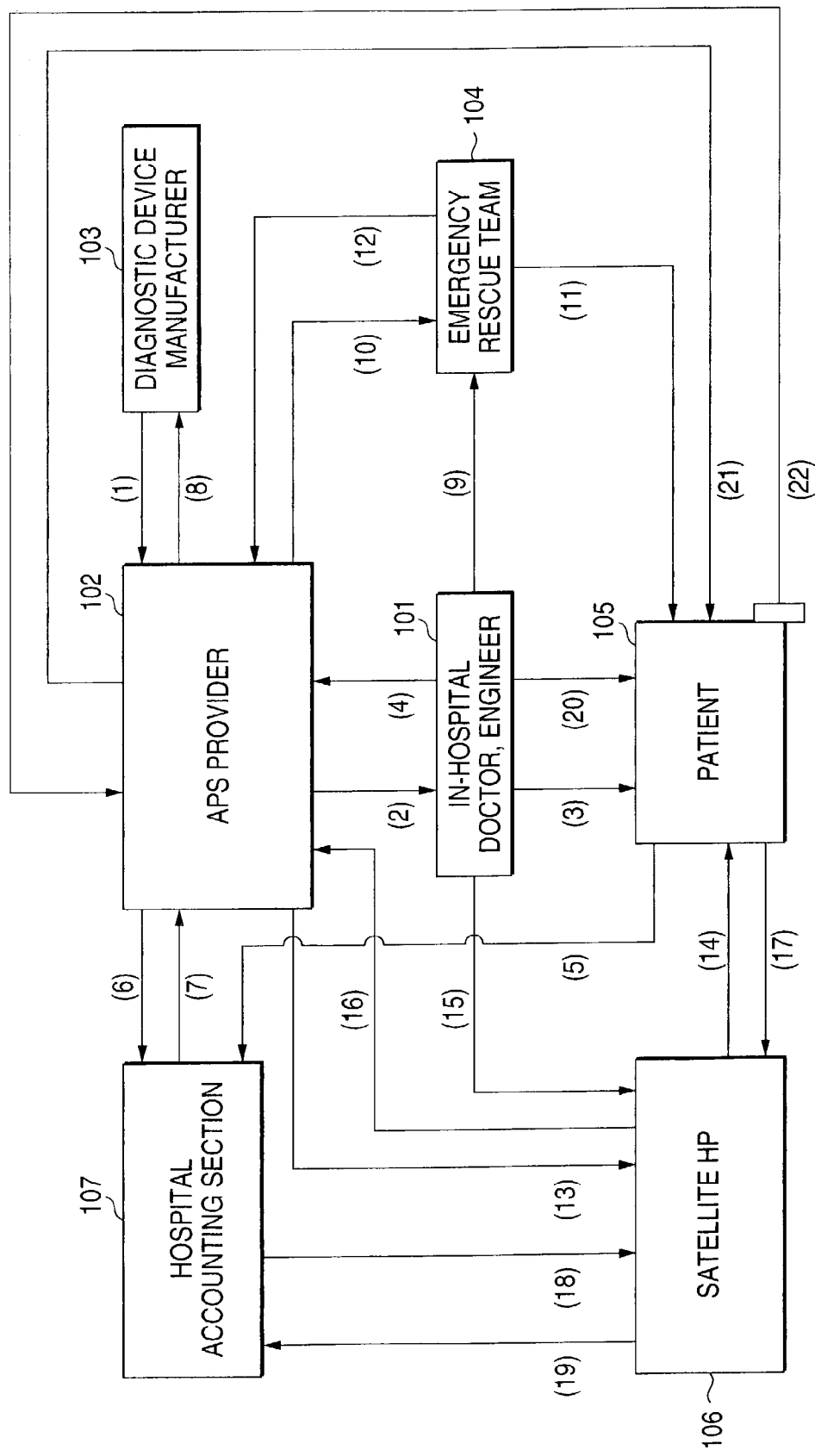
FIG. 16 is a system chart of a business model for promoting enhancement of functions according to the embodiment.

FIG. 16 is for use in illustration of a business model according to the embodiment. An in-hospital doctor/technician 101 carries out an examination (3) to a patient 105. An emergency rescue team 104 carries out an actual examination (11) to the patient 105 in the site of emergency according to instructions about examination (9) from the in-hospital doctor/technician 101. An external satellite hospital (HP) 106 carries out an examination (14) to the patient 105 according to instructions about examination (15) from the in-hospital/technician 101. The patient 105 carries out an examination (3) by himself/herself at home according to examination instructions (20) from the in-hospital doctor/technician 101. The in-hospital doctor/technician, the emergency rescue team, the external satellite hospital and the patient in the above cases are provided with necessary functions (2), (10), (13), and (21) from an ASP provider 102, and transmit count information (4), (12), (16), and (22) for charges generated by using these functions to the ASP provider 102.

The ASP provider 102 collects the count information, and transmits bills (6) to the hospital accounting section 107. Then, the fee (7) is fully paid altogether to the ASP provider 102 from the hospital accounting section 107. All or part of the fee is paid to the diagnostic device manufacturer 103 that provides function registration (1) as a fee (8). The hospital accounting section 107 bills the satellite hospital (HP) 106 that is fiscally independent from the former hospital for a function using fee (18), and the fee is collected on behalf of the provider (19). The patient 105 pays the examination fee (5), (17) to the hospital accounting section 107 and the satellite hospital 106. The system of collecting and distributing the fee for using the functions is thus established, so that the functions are more provided and more enhanced.

Figure 17:
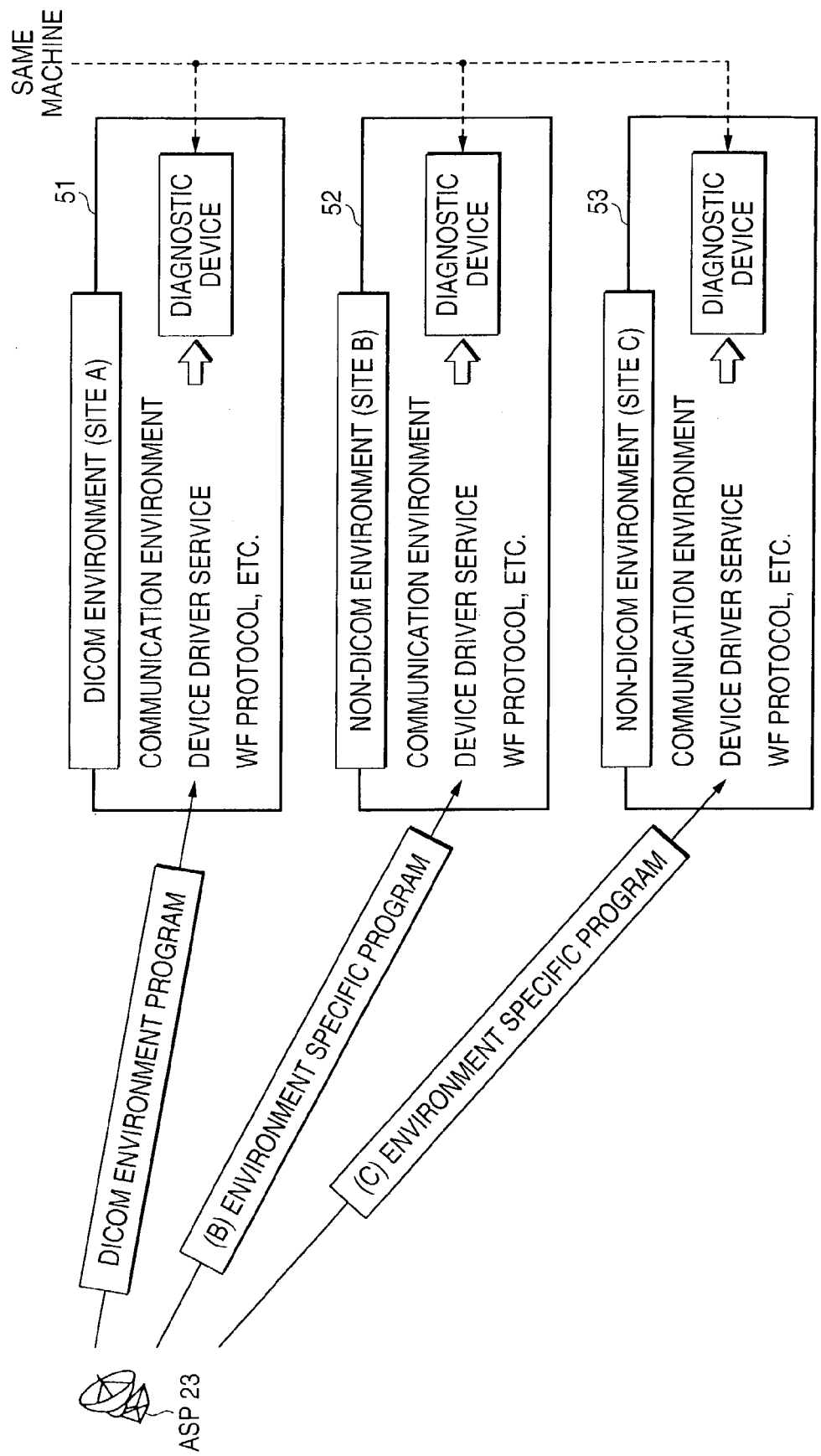
FIG. 17 is a diagram showing an example of how the transmission format is changed depending on the transmission/reception environments of facilities according to the embodiment.

FIGS. 17 and 18 show a specific example of how the transmission format is changed when the transmission/reception environment of the facility to carry out examination is different. As well known, the standard related to "Digital Imaging and Communications in Medicine" has been specified by the ACR-NEMA. There are not only a facility 51 in the DICOM environment in which the system has been configured according to the standard, but also facilities and/or users 52, 53, 54, and 55 in non-DICOM environments that do not meet the standard. The ASP 23 can provide program files in the DICOM format to the facility 51 in the DICOM environment, while it can provide program files in formats specific to the environments of the facilities 52, 53, 54, and 55 in the non-DICOM environments.

FIG. 19 shows an example of information communicated between the ASP server 23 and the diagnostic device 60, and from the diagnostic device 60 to the ASP 23 (upstream), facility information (1), user information (2), ASP specifying information (3), diagnostic device information (4), subject patient/examination information (5), function information (6), use state information (7), system information (8), trouble information (9) and the like are transmitted. Reversely from the ASP 23 to the diagnostic device 60 (downstream), used ASP information (1), function providing information (2), provided function information (3), function providing source information (4), function description information (5), fee information (6), use contract information (7) and the like are transmitted.

The ASP can be notified of how the diagnostic device is used, and automatically selects and provides an appropriate function (application) for the state. In order to log in to the ASP server 23, an identification code ID related to the facility or user is necessary, and the IC is basically transmitted by key input using a keyboard, bar code input, input with an ID card, and input by a wire according to a manual such as ID card input. Alternatively, the ID may be transmitted by wireless technology such as Bluetooth™ or GPS, or infrared radio technology such as the IrDa standards.

Figure 20:
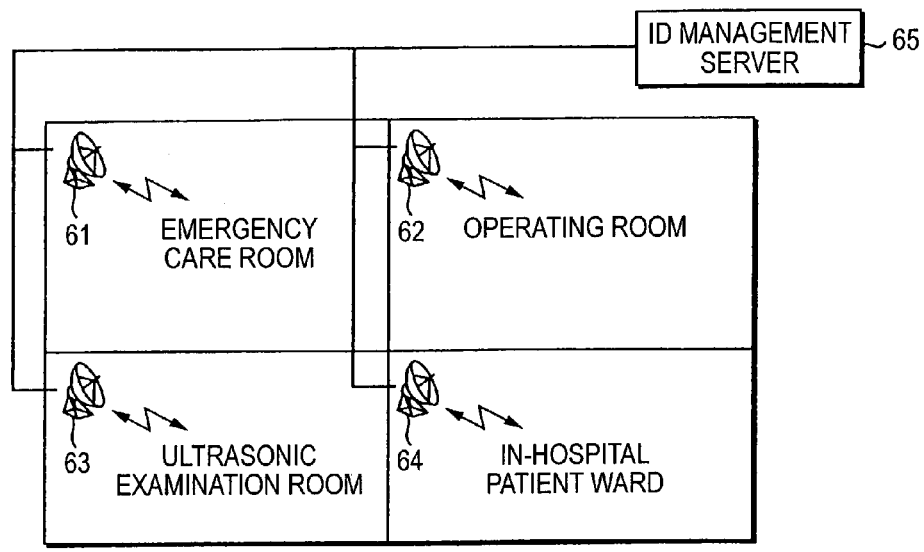
FIG. 20 shows the mechanism of notifying the ASP of how the device is used in a hospital according to the embodiment.

For use inside a building as shown in FIG. 20, by the wireless technology, equipment 61 to 64 necessary for wireless communication are provided in rooms inside the building. The ID information of the equipment 61 to 64 is transmitted from an ID management server 65 to the ASP, so that the ASP 23 can be notified of how the device is used in for example an emergency care room 61, an operating room 62, an ultrasonic examination room 63, and an in-hospital patient ward 64.

Figure 21:
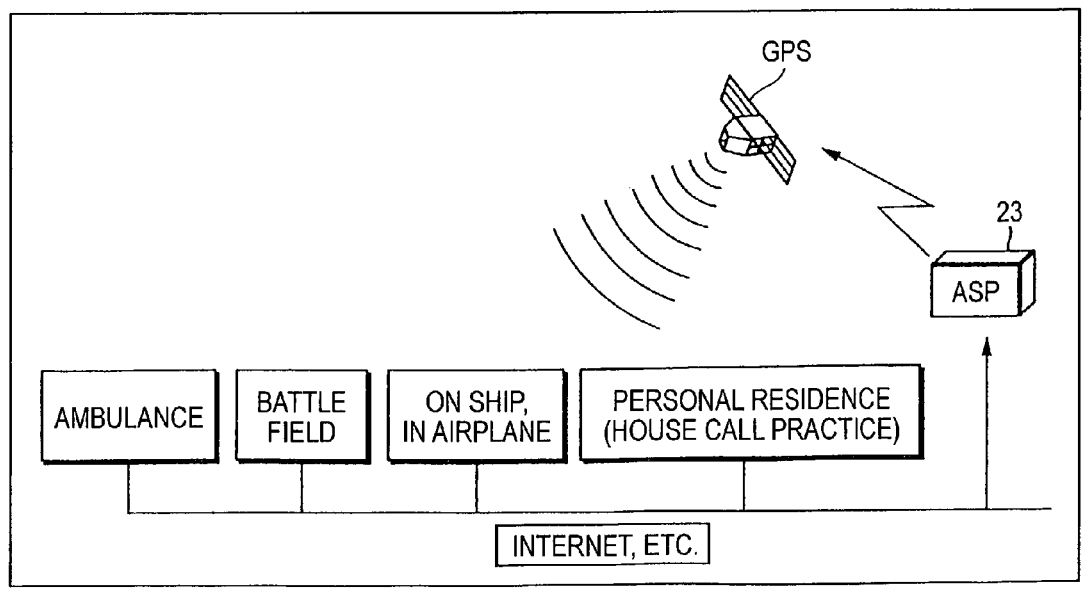
FIG. 21 shows the mechanism of notifying the ASP of how the device is used outdoors according to the embodiment.

For use outdoors, as shown in FIG. 21, the ASP 23 can be notified of how the diagnostic device is used based on GPS (Global Positioning System) information from the diagnostic device. A portable or compact, diagnostic device that can be carried is provided with necessary elements for receiving a GPS signal from a GPS satellite, the positional information transmitted from the GPS satellite is obtained to specify the location of the device at present, and the positional information is transmitted to the ASP 23. The ASP 23 is notified of the state of the location (for example whether is in an ambulance, on a battle field, on a ship, in an airplane, or in a personal residence) according to the current positional information of the diagnostic device, and the optimum function (application) for the state is selected and distributed to the diagnostic device through the GPS. Note however that via the GPS, only the downloading is enabled (one-way communication only), and therefore information from the diagnostic device to the ASP 23 is preferably transmitted through a network such as the Internet available in each location. When the device is on the move, a wireless communication network such as a mobile phone may be used. Note that there are three main circumstances in which the device could be used outdoors. In the first case, the device is provided in a vehicle such as an emergency vehicle or carried by the user in the vehicle, in the second case, the device is used in an emergency care facility on a battle field, and in the third case, the device is provided in a moving commercial vehicle such as a ship and airplane. The following points should be noted in relation to these three cases. In the first case, in response to input of the moving positional information and the vehicle ID, the ASP 23 can specify how the diagnostic device is used at present, so that an examination program file, an examination information communication protocol, and a remote instruction the most appropriate for the emergency situation, an examination result and the like can be transmitted/received. In the second case, if information cannot be transmitted from the diagnostic device, a plurality of applications transmitted from the GPS may be selectively downloaded on the device side, so that the functions of the device can be enhanced. In the third case, when the policy or charging method for treatment is changed as the vehicle crosses the border or the like between countries, applications suitable for each country are distributed. The area covered by one APS can be different among areas (countries) and as positional information and region codes are transmitted from the GPS, ASPs covering necessary areas can be utilized.

As in the foregoing, according to the embodiment, the basic functions of the diagnostic device can freely be changed and added. The functions can be changed regardless of whether they are hardware, software, or firmware. Associated information necessary for having the functions can be input as well. A business model using an ASP (Application Server Provider) as a method of providing these functions may be suggested. In this way, data such as application program files for basic functions, applied functions, and examination support functions can be downloaded to the diagnostic device from a location independent from the device depending on time to use or how to use (such as the disease, the operation environment, and the operator). Other than using the ASP, a PC card or a memory device may be used.

In this way, rather than having all the functions to cope with various different applications, only functions necessary for each situation can be provided, so that the circuit may be reduced in size and the memory may be saved. Application functions registered at an ASP or the like for each facility in advance can be downloaded, so that the mobile diagnostic device can be more convenient. In addition, when the device is used together with a workflow navigation function, one of the examination support functions, a protocol according to each situation can be loaded, and key operation can be automated or minimized according to the application. In this way, when rescue team members or nurses are not familiar with the operation of the device, operation errors can be prevented, and correct examinations can be carried out.

The invention is not limited to the above-described embodiment and may be subjected to various modifications without departing from its scope when the invention is reduced to practice. Furthermore, the above embodiment includes various stages, and various inventions can be extracted from combinations of a plurality of disclosed elements. For example, some elements may be removed from the elements of the embodiment.

As in the foregoing, according to the invention, an ultrasonic diagnostic device whose functions can be extended depending upon various environments in which the device is used, a method of extending functions related to ultrasonic diagnosis, and a method of providing extension functions related to ultrasonic diagnosis are provided.

What is claimed is:

1. A mobile ultrasonic diagnostic device for generating an ultrasonic image based on an echo signal obtained by transmitting/receiving ultrasonic waves to/from a subject body, comprising:
    an input device for inputting information identifying a class of an environment where said ultrasonic diagnostic device is used;
    a function extraction unit for extracting at least one extension function corresponding to the identified class of environment among a plurality of extension functions that can be extended at said ultrasonic diagnostic device; and
    a display unit for displaying said extracted plurality of extension functions in order to ask an operator to specify at least one desired function among said extracted plurality of extension functions.

2. The ultrasonic diagnostic device according to claim 1, wherein
    said plurality of extension functions that can be extended at said ultrasonic diagnostic device comprise at least one of ultrasonic transmission/reception sequence data, a program file for examination navigation, a program file for communication processing, a driver for peripheral equipment, a program file for measuring diagnosis, a program file for clinical examination, picture quality parameter data, and protocol data for examination navigation.

3. The ultrasonic diagnostic device according to claim 1, further comprising an interface used for entering a program file or data necessary for executing said specified extension function.

4. The ultrasonic diagnostic device according to claim 1, further comprising an access unit that accesses an external server in order to download a program file or data necessary for executing said specified extension function.

5. The ultrasonic diagnostic device according to claim 1, further comprising a slot to mount a PC card that stores a program file or data necessary for executing said specified extension function.

6. The ultrasonic diagnostic device according to claim 1, further comprising an access unit that accesses an external server in order to download a program file or data necessary for executing said specified extension function.

7. The ultrasonic diagnostic device according to claim 1, further comprising a plurality of transmitters provided in a plurality of environments where said ultrasonic diagnostic device is used for transmitting information related to said environment, and a receiver for receiving the information related to the environment transmitted from a transmitter provided in the environment where said ultrasonic diagnostic device is carried into and supplying the information to said input device.

8. The ultrasonic diagnostic device according to claim 1, further comprising a receiver for receiving information related to said environment transmitted from a transmitter provided in the environment where said ultrasonic diagnostic device is carried into and supplying the information to said input device.

9. The ultrasonic diagnostic device according to claim 1, wherein
said function extraction unit limits said extracted plurality of extension functions based on user related information input together with the information related to said environment from said input device.

10. The ultrasonic diagnostic device according to claim 1, wherein said class of environment is one of a sickroom, an operation room and an ambulance.

11. A mobile ultrasonic diagnostic device for generating an ultrasonic image based on an echo signal obtained by transmitting/receiving ultrasonic waves to/from a subject body, comprising:
an input device for inputting information identifying a class of an environment where said ultrasonic diagnostic device is used;
means for uploading said input information related to the class of environment to an external server;
means for downloading list information on a plurality of extension functions that can be used in said input environment from said external server;
a display unit for displaying said downloaded plurality of extension functions in order to ask an operator to specify at least one desired function among said downloaded plurality of extension functions; and
an access unit that accesses said external server in order to download a program file or data necessary for executing said specified extension function.

12. A mobile ultrasonic diagnostic device for generating an ultrasonic image based on an echo signal obtained by transmitting/receiving ultrasonic waves to/from a subject body, comprising:
an input device that specifies at least one desired function among a plurality of extension functions that can be used in a class of an environment where said ultrasonic diagnostic device is used;
an access unit that accesses said external server to download a program file or data necessary for executing said specified extension function; and
a storage unit that stores the program file or data downloaded from said external server.

13. A mobile ultrasonic diagnostic device for generating an ultrasonic image based on an echo signal obtained by transmitting/receiving ultrasonic waves to/from a subject body, comprising:
an access unit that accesses said external server to download a program file or data necessary for executing a plurality of extension functions that can be used in a class of an environment where said ultrasonic diagnostic device is used;
a storage unit that temporarily stores the program file or data downloaded from said external server; and
a processor that executes an extension function according to parameters set based on said stored program file or said stored data.

14. A method of extending a function for a mobile ultrasonic diagnostic device, comprising the steps of:
uploading information identifying a class of an environment where the mobile ultrasonic diagnostic device is used to an external server from the ultrasonic diagnostic device;
downloading list data for a plurality of extension functions that can be used in the class of environment where said ultrasonic diagnostic device is used from said external server;
displaying said downloaded list for the plurality of extension functions in order to ask an operator to specify at least one desired function among said downloaded plurality of extension functions; and
accessing said external server to download a program file or data necessary for executing said at least one specified extension function.

15. The method of extending a function for an ultrasonic diagnostic device according to claim 14, further comprising the steps of:
statistically adding together the period and/or the number of times for the use of said downloaded extension function; and
displaying said added result.

16. The method of extending a function for an ultrasonic diagnostic device according to claim 14, further comprising the step of:
statistically adding together the period and/or the number of times for the use of said downloaded extension function; and
uploading said added result to said external server.

17. A method of providing an extension function for a mobile ultrasonic diagnostic device, comprising the steps of:
receiving information identifying a class of an environment where said mobile ultrasonic diagnostic device is used from said ultrasonic diagnostic device;
transmitting list data for a plurality of extension functions that can be used in the class of environment where said ultrasonic diagnostic device is used to said ultrasonic diagnostic device;
receiving information to specify at least one desired function specified among said plurality of extension functions from said ultrasonic diagnostic device; and
transmitting a program file or data necessary for executing said at least one specified extension function to said ultrasonic diagnostic device.

18. The method of providing an extension function to an ultrasonic diagnostic device according to claim 17, further comprising the steps of:
receiving information related to the period and/or the number of times for the use of said at least one specified extension function from the ultrasonic diagnostic device;

statistically adding together said received information on the period and/or the number of times for the use; and transmitting said added result to said ultrasonic diagnostic device.

19. A computer implemented method of extending a function for a mobile ultrasonic diagnostic device, comprising the steps of:

uploading information related to an environment where the ultrasonic diagnostic device is used from said ultrasonic diagnostic device to an external server; and downloading a program file or data necessary for executing at least one extension function that can be used in the environment where said ultrasonic diagnostic device is used from said external server;

wherein, said downloaded program file is stored into a computer readable medium configured to extend a function of said ultrasonic diagnostic device.

20. A method of providing an extension function for a mobile ultrasonic diagnostic device, comprising the steps of:

receiving information identifying a class of an environment where the mobile ultrasonic diagnostic device is used from said ultrasonic diagnostic device;

extracting at least one extension function corresponding to said received class of environment among a plurality of extension functions that can be used by said ultrasonic diagnostic device; and transmitting a program file or data necessary for executing said extracted extension function to said ultrasonic diagnostic device.

21. A method of extending a function for an ultrasonic diagnostic device, comprising the steps of:

downloading a program file or data necessary for executing a plurality of extension functions that can be used by the ultrasonic diagnostic device from an external server in a class of an environment in which the ultrasound diagnostic device is used;

storing the downloaded program file or data necessary for executing said plurality of extension functions;

generating or processing ultrasonic image data using said stored program file or data;

displaying said generated or processed ultrasonic image data;

asking a user to refer to said displayed ultrasonic image data and select at least one necessary extension function among said downloaded plurality of extension functions; and deleting a program file or data necessary for executing extension functions other than said selected extension function.

22. A method of extending a function for a mobile ultrasonic diagnostic device, comprising the steps of:

uploading information identifying a class of an environment where the mobile ultrasonic diagnostic device is used to an external server from said ultrasonic diagnostic device to an external server;

downloading a program file or data necessary for executing a plurality of extension functions that can be used in the class of environment where said ultrasonic diagnostic device is used from said external server;

storing the downloaded program file or data necessary for executing said plurality of extension functions;

generating or processing ultrasonic image data using said stored program file or data;

displaying said generated or processed ultrasonic image data;

asking a user to refer to said displayed ultrasonic image data and select at least one necessary extension function among said downloaded plurality of extension functions; and deleting a program file or data necessary for executing extension functions other than said selected extension function.

* * * * *